United States Patent [19]

Kibblewhite

[11] Patent Number: 4,899,591
[45] Date of Patent: Feb. 13, 1990

[54] ULTRASONIC LOAD INDICATING MEMBER, APPARATUS AND METHOD

[75] Inventor: Ian E. Kibblewhite, Ambler, Pa.

[73] Assignee: SPS Technologies, Inc., Newtown, Pa.

[21] Appl. No.: 308,356

[22] Filed: Feb. 9, 1989

Related U.S. Application Data

[62] Division of Ser. No. 96,181, Sep. 11, 1987, Pat. No. 4,846,001.

[51] Int. Cl.⁴ ............................................. G01N 29/00
[52] U.S. Cl. ........................................ 73/761; 29/594; 81/429
[58] Field of Search ............ 73/761, 632, 581, 862.21, 73/2; 29/594; 310/322, 336; 173/2; 81/52, 429

[56] References Cited

U.S. PATENT DOCUMENTS

| | | | |
|---|---|---|---|
| Re. 30,183 | 1/1980 | Popenoe | 73/761 |
| 2,287,950 | 6/1942 | Tibbetts | 310/363 |
| 2,379,800 | 7/1945 | Hare | 333/24 C |
| 2,503,141 | 4/1950 | Stone | 177/311 |
| 2,600,029 | 6/1952 | Stone | 73/88.5 |
| 3,201,977 | 8/1965 | Kutsay | 73/88.5 |
| 3,306,100 | 2/1967 | Wilheim et al. | 73/67.2 |
| 3,307,393 | 3/1967 | Kessler | 73/67.1 |
| 3,308,476 | 3/1967 | Kleesattel | 73/67.1 |
| 3,541,844 | 11/1970 | Stover III | 73/88.5 |
| 3,650,016 | 3/1972 | McMaster | 29/526 |
| 3,759,090 | 9/1973 | McFaul et al. | 73/67.6 |
| 3,810,385 | 5/1974 | McFaul et al. | 73/71.5 |
| 3,812,709 | 5/1974 | Benson et al. | 73/67.5 R |
| 3,812,758 | 5/1974 | Bossler, Jr. | 85/62 |
| 3,822,587 | 7/1974 | Makino et al. | 73/67.2 |
| 3,823,639 | 7/1974 | Liber | 85/62 |
| 3,908,508 | 9/1975 | Payne | 85/62 |
| 3,918,294 | 11/1975 | Makino et al. | 73/67.2 |
| 3,924,444 | 12/1975 | Heyman et al. | 73/1 R |
| 3,930,405 | 1/1976 | Renken, Jr. | 73/71.4 |
| 3,943,819 | 3/1976 | Charron | 85/62 |
| 3,969,810 | 7/1976 | Pagano | 29/407 |
| 3,969,960 | 7/1976 | Pagano | 81/52.4 R |
| 3,975,948 | 8/1976 | Makino et al. | 73/67.2 |
| 3,987,668 | 10/1976 | Popenoe | 73/88 F |
| 4,014,208 | 3/1977 | Moore et al. | 73/67.9 |
| 4,015,464 | 4/1977 | Miller et al. | 73/61 R |
| 4,062,227 | 12/1977 | Heyman | 73/630 |
| 4,117,731 | 10/1978 | Heyman | 73/579 |
| 4,121,467 | 10/1978 | Gerhart | 73/597 |
| 4,127,788 | 11/1978 | Daugherty | 310/328 |
| 4,144,428 | 3/1979 | Voegelin | 200/159 A |
| 4,294,122 | 10/1981 | Couchman | 73/761 |
| 4,339,683 | 7/1982 | Scott et al. | 310/363 X |
| 4,344,216 | 8/1982 | Finkelston | 29/407 |
| 4,363,242 | 12/1982 | Heyman | 73/761 |
| 4,402,222 | 9/1983 | Olson et al. | 73/579 |
| 4,413,518 | 11/1983 | Jones | 73/615 |
| 4,423,634 | 1/1984 | Audenard et al. | 73/587 |
| 4,445,360 | 5/1984 | Treder, Jr. | 73/1 DV |
| 4,471,657 | 9/1984 | Voris et al. | 73/597 |
| 4,565,940 | 1/1986 | Hubbard, Jr. | 310/322 X |
| 4,567,766 | 2/1986 | Seiferling | 73/597 |
| 4,569,229 | 2/1986 | de Halleux | 73/597 |
| 4,584,676 | 4/1986 | Newman | 367/108 |
| 4,601,207 | 7/1986 | Steblay | 73/597 |
| 4,602,511 | 7/1986 | Holt | 73/581 |
| 4,633,122 | 12/1986 | Radice | 310/365 X |
| 4,676,109 | 6/1987 | Wallace | 73/761 |
| 4,760,740 | 8/1988 | Meisterling | 73/761 |

OTHER PUBLICATIONS

Final Report No. AFML-TR-78-138, "Acousto-Elastic Fastener Preload Indicator", by J. C. Couchman.

*Primary Examiner*—Jerry W. Myracle
*Attorney, Agent, or Firm*—James D. Dee; Aaron Nerenberg

[57] ABSTRACT

A method of measuring the load in a member subjected to longitudinal stress, a load measuring device and a fastener tightening device using the method of measuring, a load indicating member and a load indicating fastener for use in conjunction with the method of measuring, a method of making the load indicating fastener, a method of tightening the load indicating fastener and a transducer for instrumenting a load bearing member are each disclosed and claimed. A thin piezoelectric sensor consisting of a piezoelectric film sandwiched between two thin electrodes is permanently mechanically and acoustically coupled to the upper surface of a member and is used to determine the length, tensile load, stress, or other tensile load dependent characteristic of the member by ultrasonic techniques.

33 Claims, 7 Drawing Sheets

ULTRASONIC LOAD INDICATING MEMBER, APPARATUS AND METHOD

This is a divisional of copending application Ser. No. 096,181 filed on Sept. 11, 1987.

BACKGROUND OF THE PRESENT INVENTION

The present invention relates to load indicating members and load indicating fasteners and further relates to methods and apparatuses for making and using load indicating members and load indicating fastening members. More particularly, the present invention relates to a method of measuring a load in an ultrasonic load indicating member, a load measuring device using the method of measuring the load, a fastener tightening tool for tightening an ultrasonic load indicating fastener member using the method of measuring, an ultrasonic load indicating member and an ultrasonic load indicating fastener for use in conjunction with the method of measuring, a method making the ultrasonic load indicating fastener, a method of tightening the ultrasonic load indicating fastener, and a transducer for instrumenting the load indicating member.

In many operations, it is desirable to determine the amount of longitudinal load experienced by a longitudinally stressed member. This information is particularly useful when the longitudinally stressed member is a fastener since the measurement of the longitudinal stress provides a verification of the existence of a proper joint.

Many prior techniques have been developed to indicate the amount of longitudinal stress experienced by a fastener providing a load indicating feature on the fastener itself. This is usually done by interconnecting one end of an elongated member, such as a pin, to a portion of the fastener prior to the installation of the fastener.

Figure 1:
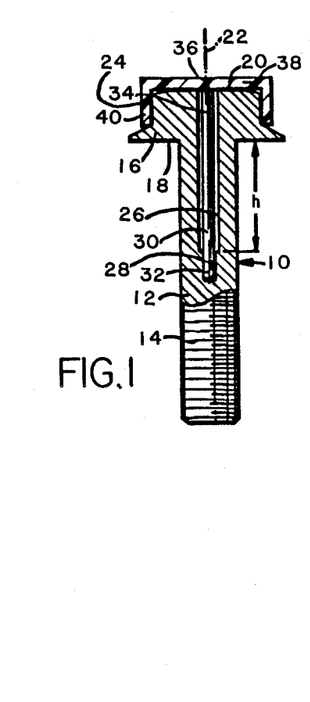
FIG. 1 is a partially cut-away side view of the load indicating member of the prior art.

An example of this type of load indicating member is depicted in FIG. 1 of the drawing. The elongated member 10 extends parallel to the fastener 12 and is unaffected by the elastic deformation of the fastener in response to longitudinal stress. The free end 14 of the elongated member 10 therefore provides a reference for indicating the elongation of the fastener 12 in response to the longitudinal stress Typically, the elongated member 10 is a pin received with in an elongated bore 16 disposed longitudinally of the fastener 12 and extended from the head 18 of the fastener and partially through the shank 20 of the fastener. One end 22 of the pin 10 is interconnected with the shank 20 of the fastener 12 at the base of the bore 16 by means, for example, of adhesives, threads, or an interference fit. The various prior load indicating members and load indicating fasteners of this type differed greatly in structure as well as in the methods and apparatuses with which they were used to provide an indication of the elongation of the load indicating member or fastener. Examples of this type of fastener are disclosed in U.S. Pat. Nos. 3,812,758 issued May 28, 1974 to Robert B. Bessler, Jr.; 3,823,639 issued July 16, 1974 to Theodore Liber; 2,503,141 issued Apr. 4, 1950 to Albert R. Stone; 3,943,819 issued Mar. 16, 1976 to Charles S. Charron; 2,600,029 issued June 10, 1952 to Albert R. Stone, 3,908,508 issued Sept. 30, 1975 to William J. Payne; 3,987,66 issued Oct. 26, 1976 to Charles H. Popenoe; and 4,144,428 issued Sept. 19, 1978 to Charles H. Popenoe; as well as in commonly assigned U.S. patent application Ser. No. 670,260 filed 11/13/84, now U.S. Pat. No. 4,676,109.

While each of the various pin-type load indicating members, and load measuring devices described above provides its own advantages in terms of accuracy, ease of manufacture, or ease of reading, they are still expensive to manufacture, since they each require extensive modifications and the addition of a centrally located pin-member to the load indicating member. As a result such load indicating members are only selectively used in practice, either where there is a specific immediate diagnostic need or a serious recognized safety hazard involved. These members are simply too expensive for routine use in assemblies which may only occasionally benefit from such monitoring.

Figure 2:
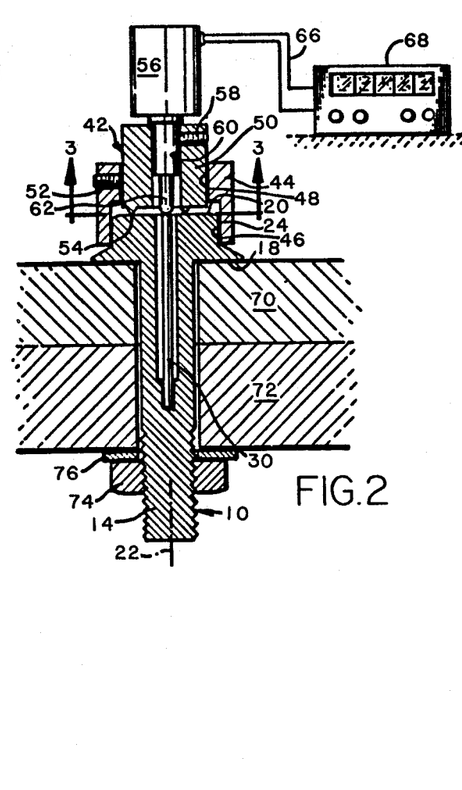
FIG. 2 is a partially cut-away side view of an ultrasonic load measuring device of the prior art.

An alternate approach to measuring the elongation of a member or fastener is to use an ultrasonic measurement device. Typically, this is done, as shown in FIG. 2 of the drawing, by removably interconnecting an ultrasonic transducer 24 to one end of the member being measured, typically to the head 26 of a fastener 28. In order to obtain a reliable indication, the head of the bolt must be ground extremely flat and a reliable ultrasonic transmission media must b applied to the head of the bolt. The transducer must be properly positioned on the bolt and held in position while the measurements are being taken. Examples of techniques and apparatuses using this method are disclosed in U.S. Pat. Nos. 3,306,100 issued Feb. 28, 1967 to Wilheim et al.; 3,307,393 issued Mar. 7, 1967 to Kessler; 3,308,476 issued Mar. 7, 1967 to Kleesattel; 3,759,090 issued Sept. 18, 1973 to McFaul et al.; 3,812,709 issued May 28, 1974 to Benson et al.; 3,822,587 issued July 9, 1974 to Makino et al.; 4,014,208 issued Mar. 29, 1977 to Moore et al.; 4,062,227 issued Dec. 13, 1977 to Heyman; 4,117,731 issued Oct. 3, 1978 to Heyman; 4,363,242 issued Dec. 14, 1982 to Heyman; 4,402,222 issued Sept. 6, 1983 to Olson et al.; 4,413,518 issued Nov. 8, 1983 to Jones and 4,471,657 issued Sept. 18, 1984 to Voris et al.

The patents teach the notion of combining the measuring device with a tightening tool so that the information gained from measuring the elongation of the bolt can be used determining when to shut off the tightening tool or, alternatively, monitor the tightening process to determine whether a proper joint has been formed. Examples of such tightening tools are disclosed in U.S. Pat. Nos. 3,969,960 issued July 20, 1976 to Pagano, 3,969,810 issued July 20, 1976 to Pagano.

While the above listed methods and apparatuses can provide reliable information about a fastener and a joint, they are in very limited use. This is mainly because the bolt must be carefully manufactured and must be easily accessible to the instrumentation. Thus, ultrasonic tension measurement is recognized as a highly accurate laboratory tightening method for calibration application testing and for tightening very critical joints. It is replacing strain gage bolts in several calibration and critical quality control applications. However, the practical difficulties associated with taking ultrasonic tension measurements described above have prevented its application as a general assembly tightening strategy.

Some attempts have been made to combine the advantages of the pin-type load indicating members, described previously, with the ultrasonic elongation measurement device described above by incorporating a piezoelectric or other ultrasonic sensor into the member itself. Examples of such members are disclosed, for example, in U.S. Pat. No. 4,127,788 issued Nov. 28, 1978 to Daugherty and U.S. Pat. No. 4,294,122 issued Oct. 13, 1981 to Couchman. Each of these disclosures provide an instrumented load bearing fastener which has been modified to incorporate a stress indicating feature. However, like the pin-type fasteners described previously, these instrumented fasteners are greatly modified in order to accept large and complicated ultrasonic sensing devices. They are therefore prohibitably expensive for wide spread use.

Examples of additional prior patents known to the applicant which teach or claim ultrasonic piezoelectric or alternate methods are:

| U.S. Pat. No. | Issue Date | Inventor |
|---|---|---|
| 3,201,977 | 8/24/65 | Kutsay |
| 3,306,100 | 2/28/67 | Wilhelm, Lyndhurst, Kliever |
| 3,307,393 | 3/7/67 | Kessler |
| 3,308,476 | 3/7/67 | Kleesattel |
| 3,541,844 | 11/24/70 | Stover |
| 3,650,016 | 3/21/72 | McMaster |
| 3,759,090 | 9/18/73 | McFaul |
| 3,810,385 | 5/14/74 | McFaul |
| 3,812,709 | 5/28/74 | Benson |
| 3,822,587 | 7/9/74 | Makino |
| 3,918,294 | 11/11/75 | Makino |
| 3,924,444 | 12/9/75 | Heyman |
| 3,930,405 | 1/6/76 | Renken |
| 3,969,810 | 7/20/76 | Pagano |
| 3,969,960 | 7/20/76 | Pagano |
| 3,975,948 | 8/24/76 | Makino |
| 4,014,208 | 3/29/77 | Moore |
| 4,015,464 | 4/5/77 | Miller |
| 4,062,227 | 12/13/77 | Heyman |
| 4,117,731 | 10/3/78 | Heyman |
| 4,121,467 | 10/24/78 | Gerhart |
| 4,127,788 | 11/28/78 | Daugherty |
| Re. 30,183 | 1/8/80 | Popenoe |
| 4,294,122 | 10/13/81 | Couchman |
| 4,363,242 | 12/14/82 | Heyman |
| 4,402,222 | 9/6/83 | Olson |
| 4,413,518 | 11/8/83 | Jones |
| 4,423,634 | 1/3/84 | Audenard |
| 4,445,360 | 5/1/84 | Treder |
| 4,471,657 | 9/18/84 | Voris |
| 4,569,229 | 2/11/85 | de Halleux |
| 4,567,766 | 2/4/86 | Seiferling |
| 4,584,676 | 4/22/86 | Newman |
| 4,601,207 | 7/22/86 | Steblay |
| 4,602,511 | 7/29/86 | Holt |

Very few actual products have resulted from these developments and their use has generally been limited to laboratory work and expensive and critical installations due to the difficulty in maintaining reliable coupling during tightening, the expense and complexity of the required equipment, and the strict control required over fastener materials and properties.

What is needed, therefore, is a low cost ultrasonic transducer permanently attached to a fastener in an inexpensive manner to provide accurate tightening information on a mass production basis. Such an ultrasonic load indicating member would permit easy interconnection with measuring or assembly tool devices and avoid the problems encountered with prior ultrasonic measuring devices in attempting to obtain a reliable acoustical coupling.

SUMMARY OF THE PRESENT INVENTION

The present invention provides a load indicating member and a load indicating fastener, as well as methods and apparatuses for the use of the load indicating member and the load indicating fastener, which combine many of the advantages, heretofore only available separately in different load indicating members or fasteners, in a single member or fastener. The present invention further provides additional features and advantages not previously available in load indicating members, load indicating fasteners, load measuring devices, and tightening tools.

The load indicating member of the present invention includes a shank subjected to elastic deformation when stressed longitudinally, and first and a second generally flat surface, each formed adjacent to one longitudinal end of the shank, the first and second flat surface being coplanar and at approximately a preselected distance apart when the shank is unstressed. A piezoelectric element permanently, mechanically and electrically interconnected with first and second electrode means is disposed on the first flat surface of the shank. The first electrode means is permanently, mechanically, electrically and acoustically interconnected with the first flat surface. The first electrode means may, for example, consist of a conductive adhesive, a metallic film, or the member itself.

In a preferred embodiment, the piezoelectric element is a thin flexible piezoelectric disk, the first and second electrode means being metallic layers deposited on opposite faces of the disk. Furthermore, in this preferred embodiment, the load indicating member is a load indicating fastener having an enlarged head and the first flat surface is formed on the head of the fastener.

The method of making a load indicating fastener according to the present invention includes the steps of providing a flat surface at one longitudinal end of a fastener, disposing first and second electrode means on opposite faces of a flexible piezoelectric element; and permanently, mechanically, electrically and acoustically interconnecting the first electrode means with the flat surface of the fastener such as to electrically isolate the second electrode means from the surface.

The load measuring device according to the present invention provides a first contact means electrically engageable with the first electrode means, second contact means engageable with the second electrode means, and an electronic measurement device responsive to electronic differential signals between the first and second electrode means such as to provide a measurement of the tensile load of the load indicating member when stressed longitudinally.

In a preferred embodiment, the piezoelectric element may also provide a driving means for producing an ultrasonic signal such as to generate the electronic differential signals. Furthermore, in a preferred embodiment, the load indicating member is electrically conductive and the first contacts mean is electrically engaged with the first electrode means indirectly by engagement of the first contact means with the load indicating member.

The tightening tool of the present invention includes first and second contact means electrically engageable, respectively, with the first and second electrode means, a load inducing means for imparting a tensile load in the load bearing member, and a load means for imparting a tensile load in the load bearing member, and a load measuring device responsive to the electrical differential signal such as to provide an accurate measurement of the tensile load.

In the preferred embodiment, the tightening tool of the present invention includes a electrically conductive fastener engagement means engageable with a load indicating fastener, a contact member engageable with a second electrode means of the load indicating fastener, a drive means imparting a torque on the fastener engagement means so as to rotatably drive the load indicating fastener, and a load measuring device responsive to the electrical differential signal received from the socket and the contact member such as to provide an accurate measurement of the tensile load of the shank of the fastener when stressed longitudinally as a result of the tightening process.

The output of the load measuring device may be used to provide a continuous reading of the instantaneous tensile load of the fastener or, alternatively, may be used to determine when the fastening operation is complete or to provide an indication of the load in a previously tightened fastener. When the load indicating member is a fastener, the load measuring device may be used simultaneously with a fastener tightening tool or, alternatively, may be incorporated directly into the fastener tightening tool. When the fastener tightening tool incorporating the load measuring device is of an automatic tightening type, the tensile load indication in the load measuring device may be combined with other parameters, monitored by the fastener tightening tool, such as angle and torque, to determine when the tightening cycle is complete and to detect irregularities in the joint.

The method of measuring the load in a load indicating member according to the present invention includes the steps of interconnecting a load measuring device of the present invention with a load indicating member of the present invention and calculating the tensile load of the shank of the load indicating member from ultrasonic measurements.

The method of tightening a load indicating fastener according to the present invention includes the steps of interconnecting a load measuring device according to the present invention to the head of a load indicating fastener according to the present invention, tightening the load indicating fastener while continuously monitoring the load measuring device to determine when a preselected load is reached, and ceasing the tightening of the load indicating fastener when the preselected load is reached, as indicated by the load measuring device.

A primary object of the present invention is to provide an inexpensive load indicating member or fastener which may be easily installed with conventional tools. Another object of the present invention is to provide an inexpensive and accurate method of measuring the load in the load indicating member or a load indicating fastener, a load indicating device and a fastener driving tool using the method of measuring of the present invention, a load indicating member for use in conjunction with the method of measuring of the present invention, a method of making the load indicating member of the present invention, and a method of tightening the load indicating fastener of the present invention.

Another object of the present invention is to provide an inexpensive method of making a reliable, accurate and compact load indicating member or fastener from a conventional member or fastener.

Another object of the present invention is to provide a transducer having improved performance including a higher signal to noise ratio than prior designed.

Yet another object of the present invention is to provide a method and an apparatus for reliably and removably coupling a load measuring device with a load indicating member or fastener and for repeatedly or continuously monitoring the load indicating member or fastener.

Still another object of the present invention is to provide a method, tool, and load indicating member providing a means for monitoring the quality of the member by detecting imperfections in the member and further inspecting members which were stressed at an earlier time to determine the current condition, and particularly, to determine if prestressed fasteners have loosened.

Yet another object of the present invention is to provide a load indicating fastener which may be tightened by conventional tightening tools and, more particularly, to provide a load indicating fastener which may be monitored by a load measuring device during a tightening operation.

Still another object of the present invention is to provide a method for providing a continuous indication of the load in a load indicating fastener during a tightening operation or during us of the device to which the fastener is attached.

Still yet another object of the present invention is to provide a fastener tightening device for use in conjunction with a load indicating fastener, which fastener device provides an automatic fastening operation responsive to a measurement of a tensile load responsive characteristic such as the shank of the load indicating fastener, during the tightening operation.

These and any other objects, features, and advantages of the present invention will become apparent to those skilled in the art when the following exemplary detailed description of the present invention is read in conjunction with the drawings appended hereto.

BRIEF DESCRIPTION OF THE DRAWINGS

In the drawings, wherein like reference numerals refer to the like elements throughout.

DETAILED DESCRIPTION OF THE PREFERRED EMBODIMENTS

Figure 3:
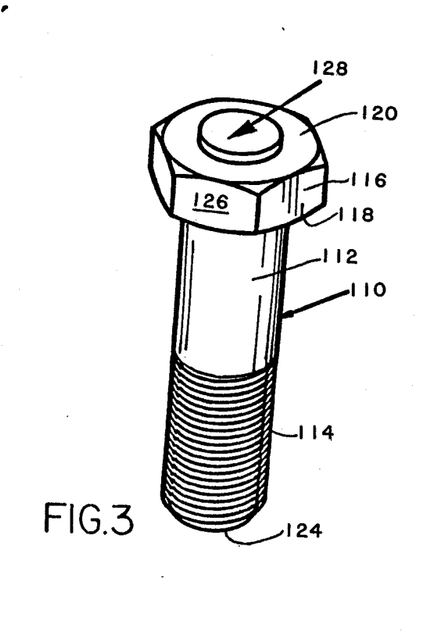
FIG. 3 is a perspective view depicting an example of a load indicating member according to the present invention.
Figure 4:
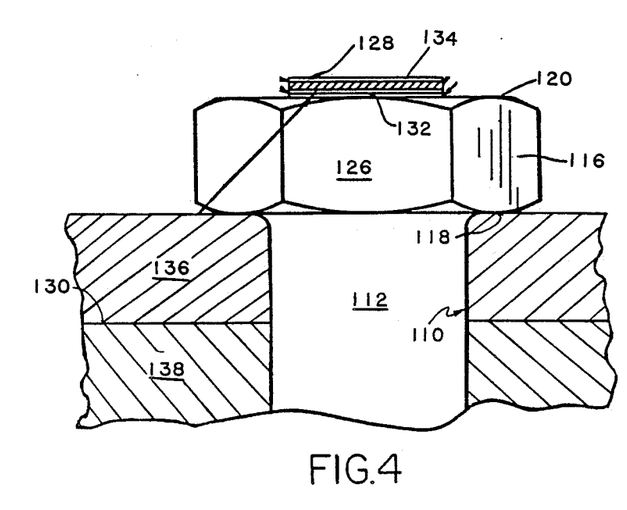
FIG. 4 is an enlarged and partially sectional view illustrating the indicating fastener of FIG. 1.
Figure 4A:
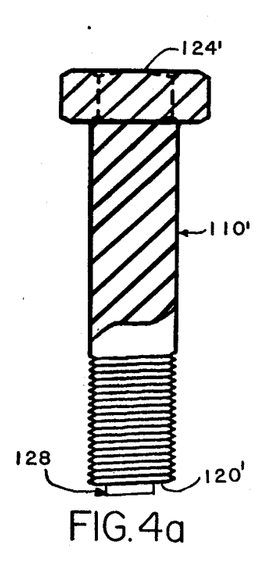
FIGS. 4a through 4c are partial views similar to FIG. 4 but illustrating alternate examples of load indicating members according to the present invention.

Referring now to the drawings and more particularly to FIGS. 3 and 4 thereof, a first example of a load indicating member, and more particularly, a load indicating fastener 110 is illustrated. The load indicating fastener 110 is formed from a conventional bolt which has been modified to provide an indication of the tensile load, stress, elongation or other characteristics of the bolt during a tightening operation as well as at various other times during the life of a joint. The bolt has a shank 112 with threads 114 formed at one end and with a head 116 formed at the other end. A shoulder 118 is formed between the head 116 and the shank 112. The head 116 has a generally flat upper surface 120 disposed normal to the longitudinal axis 122 of the shank 112. A lower surface 124 is formed at the opposite end of the shank 112 and is also disposed normal to the longitudinal axis 122. The head is also provided with a wrenching or tool engagement surface 126, such as a hexagonal wrenching surface, disposed about the periphery thereof.

Figure 4B:
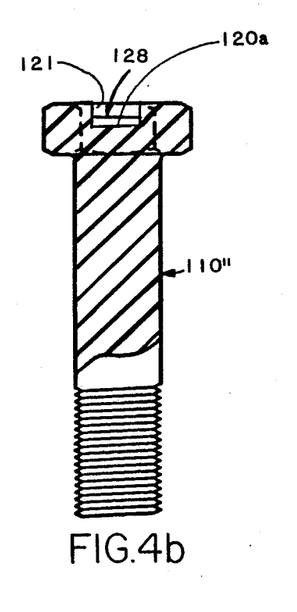
Figure 4C:
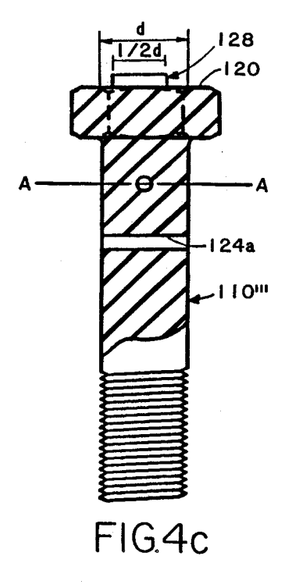

Alternatively, as shown in FIG. 4b a flat surface 120a may be formed in a recess 121 in a head 116a. The recess 121 may be a tool engagement socket or a lightening hole or a shallow recess created for the purpose of protecting the piezoelectric sensor 128 from environmental hazards.

The piezoelectric ultrasonic sensor 128 is permanently or semi-permanently mounted to the upper surface 120 or 120a of the head 116. As illustrated in the drawing, the piezoelectric sensor preferably consists of a disk 130 of piezoelectric material having a first and second electrode 132 and 134, respectively, applied to each of its opposite flat surfaces.

Preferably, the piezoelectric disk is formed of a flexible inexpensive piezoelectric material, such as a polymeric material. In the preferred embodiment polyvinylidene fluoride is chosen since it is very resistance to corrosive substances. However, other materials may exist or be developed having satisfactory properties and laminated bimorphs and multimorphs are contemplated as alternatives. The electrodes may be formed of metallic layers vacuumed deposited on the piezoelectric disk, a conductive ink or paint, or a conductive adhesive. Alternatively, one or both may be a conductive foil permanently bonded to the disk. The first electrode is electrically and acoustically coupled to the head 116 while the piezoelectric disk 130 and the second electrode 134 are electrically isolated from the head 116. For some embodiments, the head 116 will perform the function of the first electrode 132.

For some installations, the first electrode 132 may consist of a conductive adhesive. Alternatively the adhesive may be non-conductive and rely on capacitive coupling for the electrical communication between the first electrode 132 and the head 116.

In experimental work, the echo signal levels of a thin film polymeric piezoelectric transducer adhesively coupled with a member was compared with prior art thick ceramic transducers removably mechanically coupled with a member. While signal levels were comparable, the signal to noise ratio was considerably higher with the film transducer, thus demonstrating a greater ease and reliability of echo detection.

The higher noise levels of the ceramic transducer may be attributable to echoes resulting from ultrasonic waves reflected internally within the transducer and transducer housing. Reflected acoustic waves within the film transducer may decay more quickly since the lower acoustic impedance of polymeric piezoelectric films such as polyvinylidene fluoride permit more efficient transfer of energy to the air or conductive rubber contact.

It should be noted that the use of the piezoelectric film transducer therefore is a significant transducer performance improvement over the prior art.

Figure 5:
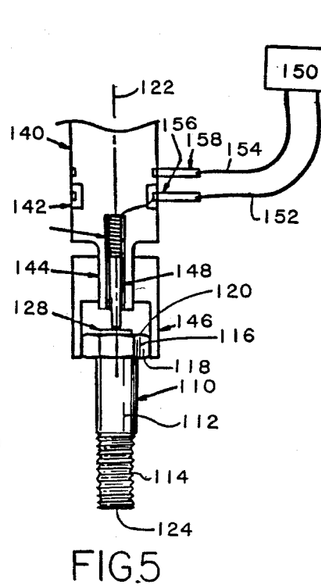
FIG. 5 is a partially schematic and partially cut-away side view depicting a load indicating fastener according to the present invention as well as a fastener tightening tool engaged therewith, the fastener tightening tool incorporating a load measuring device according to the present invention.

Referring to FIG. 5, an example of a load indicating fastener 110 described above is shown with a fastener tightening tool 140 according to the present invention engaged therewith. The fastener tightening tool 140 includes a conventional power tool 142, only the housing of which is shown in the drawing. The conventional power tool 142 has a rotary output driver 144 engageable with a socket member 146. The socket member 146 engages the head 116 of the fastener 110 both electrically and mechanically.

A contact pin 148 is reciprocally mounted to the fastener tightening tool 140 to reciprocate relative to the socket member 146 into engagement with the second electrode 134 of the piezoelectric sensor 128 and the head 116 of the fastener 110. The contact pin 148 is preferably provided with a conductive rubber tip 148a such as to provide a low acoustic impedance interface while refraining from damaging the transducer.

An electronic control device 150, shown only schematically in the drawing, is electrically interconnected with the contact pin 148 and the socket member 146 by means of electrical lines 152 and 154, respectively, by way of slip ring wipers 156 and 158, as is well-known in the art. Alternatively, the signal may be transferred by a non-contact means, such as by capacitive coupling, and other techniques well-known in the art. The electronic control device 150 supplies and measures electronic differential signals between the first and second electrodes 132 and 134 of the piezoelectric sensor 128 such as to provide an ultrasonic measurement of the tensile load, stress or elongation of the shank 112 of the fastener 110.

It will be appreciated by those skilled in the art that the fastener tightening tool 140 may be provided with a display device, not shown in the drawing, for displaying ultrasonic measurement of the tensile load, stress or elongation obtained during the fastener operation. Alternately, the fastener tightening tool 140 may be adapted to use the information continuously supplied by the electronic control device to determine when a predetermined amount of tensile load or elongation has occurred and therefore when a tightening operation should be stopped.

It will further be appreciated by those skilled in the art that the power tool chosen may, in a manner well-known in the art, monitor other characteristics of the joint being formed, such as the torque and the instantaneous angle of the load indicating fastener. An example of such a power tool may be found in the U.S. Pat. No. 4,344,216 issued Aug. 17, 1982 to Robert J. Finkleston. This other information available from the power tool may be combined with the tensile load, stress or elongation information supplied by electronic control device 150 to provide a precisely controlled tightening operation wherein the various measured parameters are used directly to control the tightening sequence or to monitor the results of the tightening operation. For example the socket member 146 may be used in conjunction with the power tool using what is known in the art as a "turn of the nut tightening sequence" while the elongation information is used subsequently to determine whether the joint formed by the tightening sequence meets certain specifications.

In use, the load indicating fastener 110 for the present invention may be used to secure panels 136 and 138 together by being passed progressively through suitable bores therein and being fastened therebehind by a nut 139. The fastener tightening tool 140 or, if desired, any standard tightening tool, engages the tool engagement surface 126 of the load indicating fastener 110 and is rotated to tighten to joint. As the panels 136 and 138 engage, respectively, the shoulder 118 and the nut 139, the shank 112 of the load indicating fastener 110 experiences longitudinal stress causing longitudinal elastic deformation of the shank 112. The amount of tensile load, stress or elongation of the shank 112 can be measured by the fastener tightening tool 140.

While FIG. 5 illustrates a fastener tightening tool 140 incorporating a convention power tool 142 and electronic control device 150, it will be appreciated by those skilled in the art that a fastener measuring tool may be made incorporating all the components of the fastener tightening tool 140 except the power tool 142. Such a device may be used to measure the elongation of a bolt independently of the tightening tool.

It should be further noted that the design of the load indicating fastener 110 described above facilitates rapid modification of existing bolts. No special surface treatment is required except the provision of a generally flat upper surface 120. In practice, it was found to be desirable with prior art methods to have a surface finish on the order of 125 micro inches while 250 micro inches has been determined to be acceptable for the purpose of acoustical coupling. However, for the present invention, a surface finish of substantially more than 250 micro inches has been found to be acceptable because of the use of an adhesive coupling. A piezoelectric sensor 128 may be formed independently of the bolt by applying a film of metallic material to each of opposite faces of a piezoelectric disk 130. A suitable adhesive for acoustically and mechanically coupling the piezoelectric sensor 128 to the upper surface 120 of the head 116 may be applied to the piezoelectric sensor in advance together with a peel-off sheet of inert material, not shown in the drawing but well-known in the art for storing the piezoelectric sensor until the time for installing the sensor on the fastener 110.

The apparatus of the present invention permits a direct measurement of the time of flight of ultrasonic waves along the axial length of the member. The time of flight will vary with the length of the bolt and with the stress in the bolt.

Many different electronic techniques for the measurement of time of flight are well-known in the art as a result of ultrasonic developments in the field of nondestructive testing. Most are capable of providing the required resolution and accuracy. However some offer advantages in terms of the number of pulses for accurate measurement, circuit complexity and power consumption.

A significant factor is that the affect of axial stress on the speed of transverse ultrasonic waves is much less than that of longitudinal waves. Therefore, measurement of the time of flight of both waves can be used to determine axial stress without knowledge of the length of the bolt. This therefore allows measurement of the axial load in pre-installed fasteners. A brief comparison of the information available from using transverse and longitudinal waves is provided below.

All ultrasonic equipment currently available uses the measurement of the time of flight of a longitudinal ultrasonic wave generated with a piezoelectric transducer mounted on one end of the bolt (usually the head). The ultrasonic wave travels to the opposite end where it is reflected back and detected by the same transducer. The numerous approaches to measuring this time of flight are briefly described below, but all produce a measurement of the change in time from the zero tension condition from which the tension is the calculated.

It is common practice to grind the ends of the fastener parallel and to a surface finish of better than 250 micro inches. A good surface finish is a requirement for adequate acoustic coupling to the bolt.

The ultrasonic wave used for this time of flight measurement may be a longitudinal wave. The particle motion in a longitudinal wave is in the direction of propagation forming moving zones of compression and tension. The time of flight of a longitudinal wave is dependent on the length of the bolt and the speed of the ultrasonic wave. The variations in the length of the bolt result from thermal expansion, elongation due to axial load as a result of tightening, and plastic deformation if tightened to yield. The speed of the ultrasonic wave is dependent on the properties of the material, that is, the composition, heat treat, and temperature, for example, and the axial stress in the fastener induced by tightening. Parameters associated with material properties and their variations with temperature are determined experimentally and normally entered into the ultrasonic tension measurement equipment along with an ambient temperature measurement.

As the fastener is tightened, the bolt extends under axial load and the speed of propagation of the ultrasonic wave is reduced due to the axial stress. The latter accounts for approximately two-thirds of the increase in the measured time of flight.

Grip length, or a preselected relevant compensating stress factor, must also be entered as a parameter when measuring tension with this technique since it affects not only the bolt elongation under load but also the average stress and hence the average speed of propagation over the length of the bolt.

There are therefore several limiting characteristics of using the time of flight of longitudinal waves over the entire length of the fastener. The measurements are dependent on grip length which must be entered as a control parameter. Additionally, variations in local stress distributions in the region of the nut affect accuracy. It is not practical to measure the tension in the fastener after it is installed unless bolts are all ground to an exact length, typically to plus or minus one ten thousandth of an inch, or the exact length is measured and entered into the measurement system as a parameter. Tension measurements are normally based on the increase in the time of flight relative to the zero load measurement made prior to commencement of tightening.

Longitudinal waves are the more commonly known sound waves in that they are the waves which are used to transmit the oscillations of a source of acoustic energy through the air to the ear. In contrast, the particles of a transverse wave do not oscillate in the direction of propagation but at right angles to it. This wave is sometimes referred to as a shear wave since adjacent particles are subject to shear forces. Since gases and liquids are generally incapable of transmitting transverse waves, a special high viscosity coupling fluid is required by prior art equipment to acoustically couple from a transducer temporarily attached to the bolt.

A longitudinal wave travels almost twice as fast as a transverse wave in steel and the time of flight is affected to a different degree by axial stress. The variation in speed of the transverse wave in response to stress is about one and one half orders of magnitude less than that of the longitudinal wave.

As described in the patent to Holt, cited in the background, longitudinal and transverse waves may be applied to one end of the fastener by a piezoelectric crystal producing a wave having both longitudinal and transverse components. The time of flight of each of the longitudinal and transverse waves is measured. The tensile stress can then be determined from these two measurements without prior knowledge of the exact length of the bolt The use of both longitudinal and transverse waves provides, in theory, two significant advantages over the use of the longitudinal wave only. Firs,, tensile load measurements can be made without first making zero load measurement i.e. load can be measured in already installed fasteners. Second, the effect of bolt to bolt variations from material properties, heat treatment etc, is reduced since they affect both longitudinal and transverse waves.

The apparatus of the present invention may be used with either or both of these waves, as contemplated by the inventor.

It is further contemplated by the inventor that the apparatus of the present invention may be used with any of the various timing techniques, including direct timing, indirect timing, clock interpolation, double pulsing, resonant frequency detection, acoustic impedance detection, harmonic frequency detection, and phase detection, as briefly described below.

Figure 6:
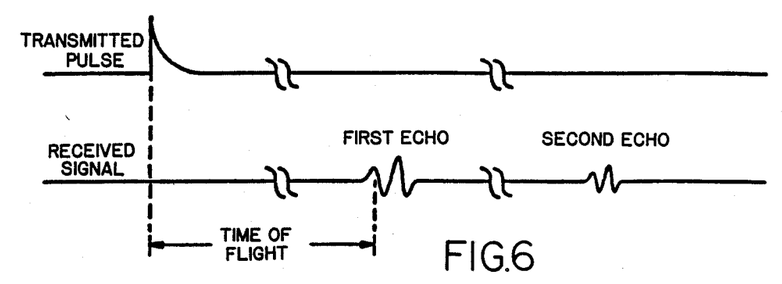
FIGS. 6 through 10 are graphical views illustrating the acoustical operation of the present invention in its various embodiments.

The direct timing technique involves measurement of the time interval from the transmission of the drive pulse to the receiving of the echo signal with a gated oscillator and counter as shown in FIG. 6. For example, one commercially available instrument sold by Raymond Engineering uses a 100 MHz clock and averages 160 measurements to achieve the required resolution. Clock rates as high as 2 GHz are now possible with Gallium Arsenide technology.

Figure 7:
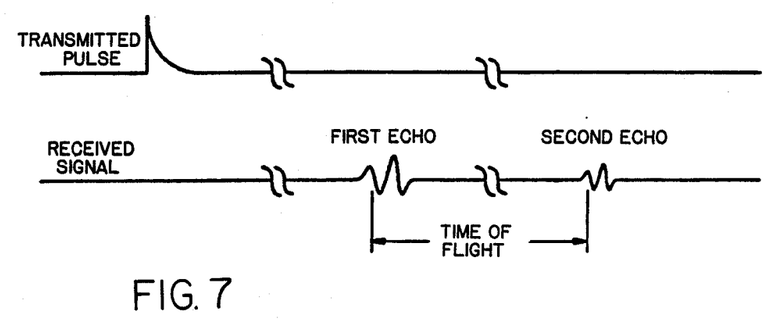

The indirect timing techniques involves timing from the first echo to the second echo as shown in FIG. 7. Measurement of the time interval between the first and second echoes eliminates errors due to trigger point variations with difference echo waveform shapes and circuit and wiring time delays. Bolt end finish is more critical since the second echo is attenuated at each of the three reflections.

Figure 8:
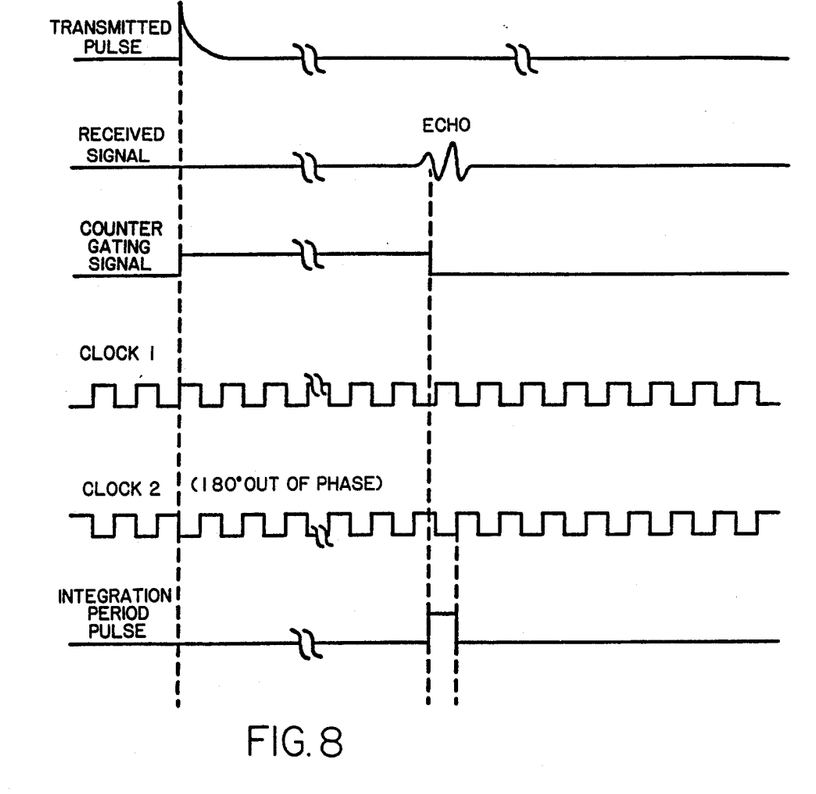

In the clock interpolation method resolution is improved by using analog techniques to determine a fraction of a clock cycle in addition to the clock count. One approach illustrated in FIG. 8, uses two synchronized out of phase clocks which are each integrated over the same short period at the end of the gating interval.

Figure 9:
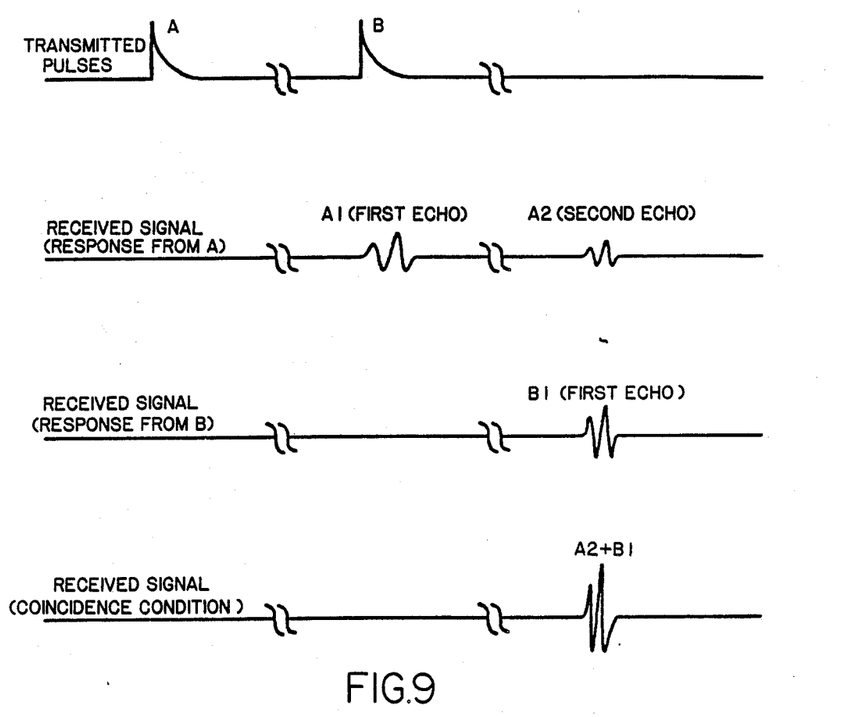

In the double pulsing technique, two pulses A and B are transmitted, as depicted in FIG. 9. Pulse A produces first echo A1 and second echo A2, and pulse B produces first echo B1 and second echo B2. The time interval between the paired pulses A and B is adjusted so that the second echo from A, i.e. A2. coincides with the first echo from pulse B, i.e. B1. The result is rectified and integrated to produce a frequency control voltage for a voltage controlled oscillator which adjusts the pulse timing. The frequency of the voltage controlled oscillator is used to calculate tension.

In the fundamental frequency detection technique, the bolt is maintained in longitudinal wave resonance at its fundamental frequency and the difference in its value before and after tightening used to determine the tension.

In the acoustic impedance detection technique the bolt is driven near its fundamental frequency and the change in mechanical or acoustic impedance used to determine tension.

The harmonic resonance frequency detection technique is a variation of the resonant method in which a harmonic longitudinal wave resonance is maintained at a harmonic frequency in for example, the 5-10 MHz range. Bolt tension is calculated from frequency shift during tightening.

Figure 10:
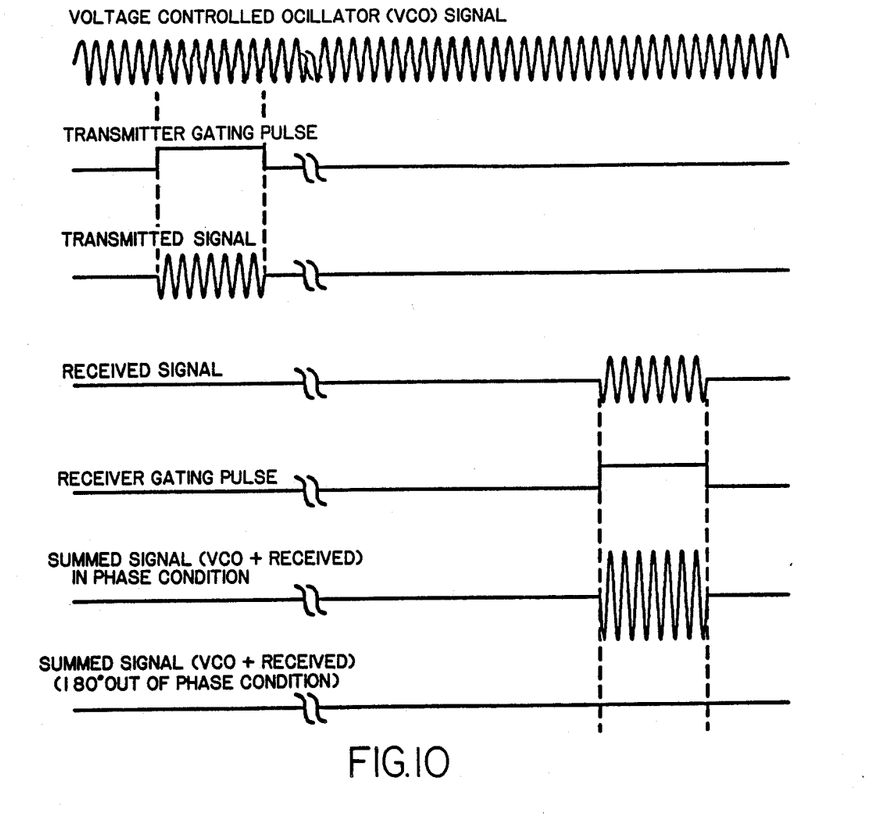

The phase detection technique uses a pulsed phase locked loop approach. The radio frequency output of a voltage controlled oscillator is periodically gated to the transducer. The received signal produced by the reflected wave is mixed with the output of the voltage controlled oscillator as shown in FIG. 10. If the oscillator and the received signal are in phase, the summed signal will be a maximum, if one hundred and eighty degrees out of phase, the two signals will cancel, forming a minimum. This summed signal, therefore represents the difference in phase and is used to control the frequency of the voltage controlled oscillator so that the phase remains constant, that is, the summed signal is a minimum or maximum. In this way, the frequency of the oscillator is adjusted so that the time of flight is maintained at an exact number of cycles. The time of flight is determined from the frequency and the number of cycles counted between the start of transmitting to the start of receiving.

It will be appreciated that the above described techniques and the two types of waves may be used in various combinations to measure one or more parameters to the desired accuracy.

It should be appreciated by those skilled in the art that the load indicating fastener 110 of the present invention facilitates the rapid interconnection of a conventional fastening tool or an instrumented fastening tool such as the fastening tool 140. Both the fastener 110 and the fastener tightening tool 140 are comparably inexpensive to manufacture use. The present invention therefore would facilitate more widespread use of ultrasonic fastening and monitoring techniques in production.

The fastener 110 and the fastener tightening tool 140 facilitate rapid formation of reliable joints having repeatable and predictable characteristics. They permit a means to detect flaws in the joint during actual installation process thus reducing the risk of catastrophic joint failure. They further permit the monitoring, at a later time, of the characteristics of the joint.

It should be noted that the fastener, method, and tool of the present invention provide an inspection feature for monitoring the condition of the load indicating member. If the approximate length of the member is known, the approximate time of flight of an ultrasonic pulse is also known. If the measured result does not agree, or if the signal is in others unlike the expected signal, there may be imperfections, such as cracks, in the member. It should also be noted that the sensor 128 can be used on either end of any bolt or threaded rod and the tool can be used in engagement with other head engagement means or with a nut engagement means.

The above detailed description includes the best mode contemplated by the inventor at the time of filing of the present application for carrying out the present invention it will be appreciated by those skilled in the art that many modifications may be made to the load indicating fastener, the load measurement device, and the fastener tightening apparatus described above without departing from the spirit of the present invention.

Such modifications are included within the intended scope of the claims appended hereto.

What is claimed as novel is as follows:

1. A method of making a load indicating fastener from a fastener having a head and a shank extending from the head, said shank being subjected to elastic deformation when stressed longitudinally such that one portion thereof moves relative to another portion thereof, said method comprising the steps of:

forming a first flat surface on said head and a location remote from said shank, said first flat surface being normal to the longitudinal axis of said shank;

forming a piezoelectric sensor by applying a first and a second electrode means to opposite faces of a piezoelectric disk; and permanently, acoustically, and mechanically interconnecting said piezoelectric sensor to said head of said fastener such as to electrically interconnect a first electrode of said piezoelectric sensor with said head and, further, such as to isolate said second electrode from said head.

2. The method of claim 1 wherein said flat surface has a surface finish of approximately more than 250 micro inches.

3. The load indicating member made according to the method of claim 1.

4. The method of claim 1 wherein said electrodes are formed by vapor deposition, electrodeposition or metallic painting.

5. The method of claim 1 wherein said first electrode means comprises a electrically and acoustically conductive adhesive.

6. A load measuring device for use in conjunction with a load indicating member having a shank, a first flat surface formed adjacent one longitudinal end of said shank, and a piezoelectric transducer secured to said first flat surface, said load measuring device comprising:

first contact means selectively engageable with said load indicating member;

second contact means selectively engageable with said piezoelectric transducer; and measurement means responsive to the electronic differential between said first and second contact means such as to provide a measurement of a tensile load dependant characteristic of said shank when said shank is stressed longitudinally.

7. The load measuring device of claim 6 wherein said load indicating member further comprises first engagement means formed at one end of said shank, said load measuring device further comprising:

second engagement means selectively engageable with said first engagement means when said load measuring device is used in conjunction with said load indicating member such as to axially position said contact means relative to said piezoelectric transducer.

8. The load measuring device of claim 7 wherein said second engagement means comprises said first electrical contact means.

9. The load measuring device of claim 8 wherein said indicating member comprises a fastener having a head formed at one end of said shank, and said first engagement means comprises tool engagement means formed on said head;

and further wherein:

said second engagement means of said load measuring device further comprises tool means selectively engageable with said tool engagement means such that said fastener is selectively rotated by rotation of said tool means.

10. The load measuring device of claim 9 further comprising:

interconnection means for interconnecting said tool means with wrenching means such as to selectively impart a rotational motion to said fastener to install and to remove said fastener while measuring said tensile load dependant characteristic thereof.

11. The load measuring device of claim 10 wherein said measurement means provides an output signal indicative of the elongation of said shank and further wherein said load measuring device further comprises:

commutator means for communicating said output signal to said wrenching means.

12. The load measuring device of claim 10 wherein said tensile load dependant characteristic comprises stress, elongation, strain or tensile force.

13. The load measuring device of claim 10 wherein said measurement means detects a first signal indicative of a transverse wave and a second signal indicative of an longitudinal wave and combines said first and second signal to determine said tensile load dependant characteristic.

14. The load measuring device of claim 13 wherein said measurement means applies the direct timing, indirect timing, double pulsing, clock interpolation, fundamental frequency detection, acoustic impedance, harmonic resonance detection, or phase detection technique to determine said tensile load dependant characteristic.

15. The load measuring device of claim 10 wherein said measurement means applies the direct timing, indirect timing, double pulsing, clock interpolation, fundamental frequency detection, acoustic impedance, harmonic resonance detection, or phase detection technique to determine said tensile load dependant characteristic.

16. The load measuring device of claim 6 wherein said tensile load dependant characteristic comprises stress, elongation, strain or tensile force.

17. The load measuring device of claim 16 wherein said measurement means detects a first signal indicative of a transverse wave and a second signal indicative of an longitudinal wave and combines said first and second signal to determine said tensile load dependant characteristic.

18. The load measuring device of claim 17 wherein said measurement means applies the direct timing, indirect timing, double pulsing, clock interpolation, fundamental frequency detection, acoustic impedance, harmonic resonance detection, or phase detection technique to determine said tensile load dependant characteristic.

19. The load measuring device of claim 6 wherein said measurement means detects a first signal indicative of a transverse wave and a second signal indicative of an longitudinal wave and combines said first and second signal to determine said tensile load dependant characteristic.

20. The load measuring device of claim 6 wherein said measurement means applies the direct timing, indirect timing, double pulsing, clock interpolation, fundamental frequency detection, acoustic impedance, harmonic resonance detection, or phase detection technique to determine said tensile load dependant characteristic.

21. The load measuring device of claim 20 wherein said tensile load dependant characteristic comprises stress, elongation, strain or tensile force.

22. A method of tightening a load indicating fastener of the type having a shank subject to elastic deformation when stressed longitudinally, a head formed at one longitudinal end of said load indicating fastener, a first flat surface formed adjacent said head, tool engagement means formed on said head adjacent said first flat surface, piezoelectric sensor means permanently mounted on said first flat surface, and a second flat surface formed at the other longitudinal end of said shank, said method comprising the steps of:

engaging a tightening tool with said tool engagement means;

engaging contact means with said piezoelectric sensor;

operating said tightening tool to tighten said load indicating fasteners; and measuring a signal representative of the time of flight of an ultrasonic wave along said shank by monitoring the differential electronic signal between said tool engagement means and said contact means such as to provide a continuous measurement of the tensile load of said shank during the operation of said tightening tool.

23. The method of claim 22 wherein said step of operating said tightening tool further comprises rotating said tightening tool until the occurrence of a condition measured by said tightening tool indicative of a proper joint, said method further comprising the step of:

verifying the existence of a proper joint using said measurement of said tensile load dependant characteristic.

24. The method of claim 22 further comprising the step of:

ceasing operation of said tightening tool when said measuring step indicates that a predetermined level of said tensile load dependant characteristic is measured.

25. The method of claim 24 wherein said tensile load dependant characteristic comprises stress, elongation, strain or tensile force.

26. The method of claim 24 wherein said step of measuring a signal further comprises detecting a first signal indicative of a transverse wave and a second signal indicative of an longitudinal wave and combining said first and second signal to determine said tensile load dependant characteristic.

27. The method of claim 24 wherein said steps of measuring a signal applies the direct timing, indirect timing, double pulsing, clock interpolation, fundamental frequency detection, acoustic impedance, harmonic resonance detection, or phase detection technique to determine said tensile load dependant characteristic.

28. The method of claim 27 wherein said tensile load dependant characteristic comprises stress, elongation, strain or tensile force.

29. The method of claim 28 wherein said step of measuring a signal further comprises detecting a first signal indicative of a transverse wave and a second signal indicative of an longitudinal wave and combining said first and second signal to determine said tensile load dependant characteristic.

30. The method of claim 22 wherein said two engaging steps occur simultaneously, said tool engagement means being fixedly interconnected with said tightening tool and said contact means being reciprocably interconnected with said tool engagement means.

31. The method of claim 22 wherein said tensile load dependant characteristic comprises stress, elongation, strain or tensile force.

32. The method of claim 22 wherein said step of measuring a signal further comprises detecting a first signal indicative of a transverse wave and a second signal indicative of an longitudinal wave and combining said first and second signal to determine said tensile load dependant characteristic.

33. The method of claim 22 wherein said step of measuring a signal applies the direct timing, indirect timing, double pulsing, clock interpolation, fundamental frequency detection, acoustic impedance, harmonic resonance detection, or phase detection technique to determine said tensile load dependant characteristic.

* * * * *